US012655081B2

(12) United States Patent
Ansovini et al.

(10) Patent No.: US 12,655,081 B2
(45) Date of Patent: *Jun. 16, 2026

(54) PROCESS FOR PRODUCING GLYCOLS FROM CARBOHYDRATES AND BURNING WASTE

(71) Applicant: Avantium Knowledge Centre B.V., Amsterdam (NL)

(72) Inventors: Davide Ansovini, Amsterdam (NL); Benjamin McKay, Amsterdam (NL); Jagdeep Singh, Amsterdam (NL)

(73) Assignee: Avantium Knowledge Centre B.V., Amsterdam (NL)

( * ) Notice: Subject to any disclaimer, the term of this patent is extended or adjusted under 35 U.S.C. 154(b) by 550 days.

This patent is subject to a terminal disclaimer.

(21) Appl. No.: 18/027,836

(22) PCT Filed: Sep. 27, 2021

(86) PCT No.: PCT/EP2021/076506
§ 371 (c)(1),
(2) Date: Mar. 22, 2023

(87) PCT Pub. No.: WO2022/064037
PCT Pub. Date: Mar. 31, 2022

(65) Prior Publication Data
US 2023/0331648 A1 Oct. 19, 2023

(30) Foreign Application Priority Data
Sep. 28, 2020 (EP) ..................................... 20198770

(51) Int. Cl.
*C07C 29/16* (2006.01)
*B01J 23/30* (2006.01)
*C07C 29/84* (2006.01)

(52) U.S. Cl.
CPC ............... *C07C 29/16* (2013.01); *B01J 23/30* (2013.01); *C07C 29/84* (2013.01)

(58) Field of Classification Search
CPC ......... C07C 29/16; C07C 29/84; C07C 29/60; C07C 29/132; C07C 31/202; C07C 31/205; C07C 31/225; B01J 23/30
See application file for complete search history.

(56) References Cited

FOREIGN PATENT DOCUMENTS

| | | |
|---|---|---|
| CA | 1067061 A | 11/1979 |
| CN | 102643165 A | 8/2012 |
| CN | 106866372 B | 8/2020 |
| NO | 2021122853 A1 | 6/2021 |
| WO | 2015150250 A1 | 10/2015 |
| WO | 2016091751 A1 | 6/2016 |
| WO | 2016097064 A1 | 6/2016 |
| WO | 2016114661 A1 | 7/2016 |
| WO | 2016162316 A1 | 10/2016 |
| WO | 2017042125 A1 | 3/2017 |
| WO | 2017050847 A1 | 3/2017 |
| WO | 2017202727 A1 | 11/2017 |
| WO | 2017202731 A1 | 11/2017 |
| WO | 2019162260 A1 | 8/2019 |

OTHER PUBLICATIONS

International Search Report and Written Opinion mailed Jan. 11, 2022 for PCT/EP2021/076506.

*Primary Examiner* — Jafar F Parsa
(74) *Attorney, Agent, or Firm* — Suiter Swantz IP

(57) ABSTRACT

A process for producing glycols from a carbohydrate source using a catalyst system, and which process can be carried out continuously in a reactor, and in which process a catalyst material is recovered from the reactor effluent. The reactor effluent is subjected to separation to obtain some valuable glycols, and one or more of the bottom streams comprising heavy polyols and some catalyst material containing one or more tungsten compounds is subjected to burning, and the burner is part of a boiler that can generate steam. Such steam may be used in the separation of one or more of the desired compounds.

20 Claims, No Drawings

PROCESS FOR PRODUCING GLYCOLS FROM CARBOHYDRATES AND BURNING WASTE

INTRODUCTION

The present invention relates to a process for producing glycols from a carbohydrate source using a catalyst system, and which process can be carried out continuously in a reactor, and in which process a catalyst material is recovered from the reactor effluent. More specifically, this invention relates to a process in which the reactor effluent is subjected to separation to obtain some valuable glycols, and one or more of the bottom streams comprising heavy polyols and some catalyst material containing one or more tungsten compounds is subjected to burning, and the burner is part of a boiler that can generate steam. Such steam may be used in the separation of one or more of the desired compounds. The tungsten catalyst compounds can be recovered from the ash, and energy from the burning can be recovered.

BACKGROUND OF THE INVENTION

WO 2016/114661 discloses a continuous process for preparation of ethylene glycol from a carbohydrate source. Said process is carried out in a stirred tank reactor (CSTR) in which a catalyst system is present. Said catalyst system comprises a tungsten compound and at least one hydrogenolysis metal. The hydrogenolysis metal is preferably present in the form of a catalyst supported on a carrier. Such heterogeneous catalyst particles can fairly easily be separated from the effluent stream e.g. by a sieve plate and added back. The tungsten compound on the other hand is generally present dissolved or dispersed in the liquid reaction medium and not so easily removed from the effluent stream. Hence, the tungsten compound is partly removed as part of the effluent in operating the process. In order to maintain a desired concentration of the tungsten compound, it is thus needed that continuously or periodically the required tungsten compound is added to the reactor (next to carbohydrate source, diluent and hydrogen). This is what is done in the process of WO2016/114661.

Next to ethylene glycol other alkylene glycols such as 1,2-propylene are produced which can also be valuable, and furthermore polyols are generally obtained in varying amounts, such as glycerol, sorbitol, erythritol and others. Depending upon market price, amount formed, and ease of recovery one or more of such polyols may also be (at least partially) be recovered. Sorbitol and erythritol are generally considered as "heavy polyols" that are obtained in such processes, as these are higher boiling. Commercial value and difficulty in obtaining them in desired purity makes that that these are usually not isolated separately.

Glycerol may also be produced in substantial quantities, and although also quite high boiling: it is commercial value may mean it is isolated in pure enough form from the products, although usually part of the glycerol will remain.

CN 102643165A discloses a process for producing ethylene glycol (and 1,2 propylene glycol) from sugars by a continuous process through hydrocracking of the sugars using hydrogen and a catalyst system. The reactor effluent is separated into product streams using rectification to obtain the desired products, and at least part of the heavy polyols that are produced are in this process are recycled back to the reactor, together with unreacted sugars.

A variant of the process of the above reference with recycle is disclosed in WO 2017/042125 in which (what is in that reference called a hydrocarbon heavies stream) is partially recycled back to the reactor (e.g. to reuse the homogeneous catalyst), whilst the other part is taken as a bleed stream and subjected to thermal oxidation at a temperature of 300-750° C. This thermal oxidation yields a solid residue that can be collected from it. The solid residue may contain a compound containing tungsten, molybdenum, lanthanum or tin.

Whilst the processes of CN 102643165A and WO 2017/042125 allow re-using the homogeneous catalyst and ensure that there is a continuous flow of homogeneous catalyst into the reactor (to balance what goes out with the reactor product stream), the recycling also brings heavy polyols (e.g. erythritol and sorbitol, which are obtained as side products) back into the reaction loop. There is a danger that these heavy polyols and/or their degradation products build-up (even with a bleed), and given that it is a mixture of products the recycle, the exact composition in the reactor is difficult to control or predict, and thus process control gets more complex.

A process like that of WO2016/114661 and of CN 102643165A aim to produce products like ethylene glycol and/or propylene glycol from renewable sources like sugars and other carbohydrates, and so-produced ethylene glycol and/or propylene glycol is intended as a sustainable alternative to producing ethylene glycol and/or propylene glycol from fossil sources. These processes based on renewable carbohydrates, however, stand little chance of being implemented if the cost per tonne of ethylene glycol (MEG) or propylene glycol (PEG) is way too high, compared to that of such components produced from fossil sources. Part of the cost-disadvantage of MEG or PEG produced from renewable sources like carbohydrates comes stems from the process being relatively new, not fully developed, whereas the process for producing MEG or PEG from fossil sources is well engineered over decades. This means that there is an economic challenge for the processes of WO2016/114661 and of CN 102643165A: they will only succeed if cost of production of MEG or PEG per tonne is kept within limits. Apart from new and little proven processes, part of the cost disadvantage of producing MEG and/or PEG from sustainable sources with the processes like WO2016/114661 and of CN 102643165A comes from the extensive purification that is needed. The process produces a mixture of compounds ("product soup"), with next to MEG and PEG (which also need to be separated from each other!) other glycols and diols like butanediols and pentanediol being formed, but also polyols like glycerol, erythritol, and sorbitol. Yet a third factor that contributes to an economic disadvantage of producing MEG and/or PEG from carbohydrates is that the reaction occurs in a reaction medium that is largely water, as usually water is needed to dissolve the sugars. All this water needs to be separated from the desired MEG and PEG.

Removing of water from the product mixture that comes out of the reactor is generally believed to be best done by evaporators. Separating the desired products from the product soup as described above is generally foreseen to be achieved with multiple distillation steps. Such distillation steps are e.g. described in WO2015/150250, WO2016/091751, WO2016/097064, WO2016/162316, WO2017/050847, WO2017/202727, WO2017/202731, WO2019/162260, and WO2021/122853. These distillation steps usually require feeds to be heated, e.g. to temperatures above 140° C. None of these documents has addressed this, but if the energy for this will be taken from the grid, most likely the processes to produce MEG and/or PEG with such distillation (and evaporation) steps will not be cost competitive with MEG or PEG from fossil sources, and/or will not be commercially attractive.

Hence, there is a need for a process for producing ethylene glycol and/or propylene glycol in a continuous manner (as such is most economical) from a reaction of carbohydrates with hydrogen in the presence of a catalyst system, preferably with good selectivity for ethylene glycol and/or 1,2-propylene glycol, preferably in high yields, which process is preferably practical to implement on a commercial scale, and in which process there is no risk of build-up of polyols like erythritol and/or sorbitol or their degradation products. Preferably, the process would need to be attractive from an economical point of view, e.g. in terms of energy requirement or energy conservation. Preferably also in such process the homogeneous tungsten catalyst material can be recovered from the reactor effluent easily, e.g. for potential regeneration of the catalyst.

SUMMARY OF THE INVENTION

It has now been found that such can be achieved, at least in part by a process for producing ethylene glycol and/or propylene glycol and/or glycerol in a continuous manner from a feed to a reactor, the feed comprising a carbohydrate source in an aqueous liquid, hydrogen, and a co-catalyst comprising a tungsten-containing compound, said reactor comprising a further co-catalyst comprising a metal selected from the groups 8, 9 or 10 of the Periodic Table of Elements, wherein the flow out of the reactor comprises water, the tungsten-containing compound, one or more of ethylene glycol, propylene glycol, glycerol, and one or more polyols other than glycerol, wherein said flow out of the reactor is subjected to the following process steps:
  - a. separating ethylene glycol and/or propylene glycol and/or glycerol from the flow out of the reactor to yield ethylene glycol and/or propylene glycol and/or glycerol and one or more bottom streams and one or more tungsten-containing compounds,
  - b. subjecting said bottom streams of distillation stages to a burner in which the polyols are burned at a temperature of above 900° C.,
  - c. recovering ash comprising a tungsten-containing compound from one or more of: the burner, ancillary parts of the burner, the exhaust gas,
  - d. recover at least part of the tungsten-containing compound from the recovered ash obtained by step c.,
wherein said burner is part of a boiler system to generate steam from water.

It was found that burning of the polyols that remain after isolating desired products like ethylene glycol and/or propylene glycol and/or glycerol from a process of making alkylene glycols from carbohydrates is in fact an attractive way to deal with it, even though it is a substantial amount. Reason is that these polyols can be burned in a boiler that can be used to generate steam, and such steam can easily be used in the separation processes for isolating the desired products ethylene glycol and/or propylene glycol and/or glycerol, and/or the evaporation of water from the product stream. This is in particular the case wherein ethylene glycol and/or propylene glycol and/or glycerol are obtained by (a series of) distillation steps. Such distillation requires heating, e.g. by steam, which thus may be generated by the process itself, making it economically attractive. Such burning then also forms an easy outlet for e.g. some volatile alcohols that may be produced by the process, as well as any gaseous components such as excess hydrogen or methane formed. Yet a further advantage is that the homogeneous tungsten catalyst usually employed as part of the catalyst system can relatively easily be recovered from the ash produced in the burner, optionally needing regeneration.

Glycerol may be one of the desired products to be isolated, e.g. by distillation, depending e.g. on demand and market price. However, it may be beneficial if not all glycerol produced is isolated by distillation, but part is left to be part of the bottom stream, which is to be burned in a burner/boiler. The amount of glycerol to be send to the burner/boiler may be e.g. from 5 to 100% of the glycerol produced, but is preferably from 5 to 50%, more preferably from 5 to 30%, even more preferably from 5 to 20% by weight of the glycerol produced in the reactor.

It is stated in the process according to this invention that ash comprising a tungsten-containing compound from one or more of: the burner, ancillary parts of the burner, the exhaust gas may be recovered. Herein, "tungsten-containing compounds from the exhaust gas" encompasses tungstic acid and tungstate salts and tungsten oxides as far as they are not deposited as ash in the burner or ancillary parts of the burner but are part of the exhaust gas. The ash components may be present as a solid (particulate) ash, which solid ash may deposit on a burner or inside a burning chamber. These components may also be deposited in the exhaust system or other ancillary parts of the burner/boiler system, or they may be very fine solids part of the exhaust gas, to be recovered by means known in the art, e.g. filters and electrostatic devices. Herein, "ancillary parts of the burner" encompass parts of the burner/boiler housing and chimney or exhaust where ash deposits form when burning the effluent of the reactor for the types of reactions discussed above.

DETAILED DESCRIPTION OF THE INVENTION

The term "polyol" is herein understood as to mean an organic molecule with more than two hydroxyl groups.

"Continuous process" and "continuous manner" is herein to be understood as not a batch process. It takes place in a reactor system with at least one feed, and at least one product stream, and is intended to run in steady state (after start-up). Duration (from start-up to stopping the reaction) is preferably at least 5 times the average residence time of the reactor system, more preferably at least 10 times the average residence time, most preferably at least 50 times the average residence time.

In the process according to the present invention, desired products like ethylene glycol and/or propylene glycol and/or glycerol are preferably obtained from the stream produced by the reactor by distillation, preferably by a series of distillation steps. Such series of distillation steps preferably employs 2 to 8 distillation steps.

In the present reaction, the steam generated by the boiler may be used in the distillation of one or more of the desired products. Hence, in the present invention it is preferred that the steam generated in the boiler is used in the separation of the ethylene glycol and/or propylene glycol and/or glycerol of the flow out of the reactor, preferably by using the steam in distillation of one or more of ethylene glycol and/or propylene glycol and/or glycerol from the flow out of the reactor.

Apart from the desired products and polyols, the flow out of the reactor will contain water volatile alcohols, such as methanol and/or ethanol. Preferably, such water and volatile alcohols are removed prior to obtaining the desired products like EG and PG by distillation. Hence, in the process according to the present invention it is preferred that prior to or during step a. volatile alcohols comprising ethanol and/or methanol are removed from the flow out of the reactor, which volatiles are also fed to the burner of step b. Likewise, in the process according to the present invention it is preferred that prior to step a. water is removed from the flow out of the reactor system by evaporation.

The distillation of the product stream to yield desired compounds like ethylene glycol and/or propylene glycol may also yield a stream containing an azeotrope, e.g. of ethylene glycol and a butanediol, e.g. 1,2-butanediol. Preferably, such azeotrope is also burned in step b, as the energy such generates may be more beneficial than trying to separate the azeotrope. Hence, in the present invention, it is preferred that the azeotrope of ethylene glycol and 1,2-butanediol that is formed during or after step a. is fed to a burner, preferably the same burner as the burner in step b.

Apart from generating steam by burning the waste stream (which steam can be utilized in e.g. distillation of desired products and/or evaporation of water from the product stream of the reactor) the process according to the present invention has the advantage that the homogeneous catalyst (here: tungsten-containing compound) that is obtained in the effluent of the reactor can be recovered fairly easily, by collecting ash during/after burning step b. Such homogeneous catalyst (here: tungsten-containing compound) that is obtained in the effluent of the reactor) can conveniently remain in the main stream whilst water is evaporated off and/or when volatile alcohols are removed, and/or when desired products are distilled off, ending up in the polyol-containing bottom stream. When such polyol-containing bottom stream (thus also containing the tungsten-containing compound) is burned, a tungsten-containing compound can be found in ash that may deposit in or on the burner and/or ancillary parts of the burner and/or in the exhaust gas. Such tungsten-containing compound is preferably recovered from such ash, and (optionally after regeneration) and optionally after solubilisation in a suitable liquid, can be ready for reuse in the process (feeding back to the reactor). Hence, it may be preferred that in the process according to the present invention that the tungsten-containing compound recovered from the ash is regenerated and solubilised in a liquid for feeding back to the reactor.

In the above, it is stated that the tungsten-containing compound is solubilized in a liquid for feeding back: this is done as such liquid is easier to handle and dose and disperse in the reactor than a solid matter. Solubilisation is preferably done in a suitable liquid. Depending on the nature of the tungsten-containing compound, this is as such or after regeneration. A preferred liquid for such solubilisation comprises an alkylene glycol. Hence, in the present invention it is preferred that the liquid in which the regenerated tungsten-containing compound is solubilized comprises alkylene glycol, preferably ethylene glycol and/or propylene glycol. This has the advantage that no foreign liquids are introduced in the system, and such alkylene glycols are ready at hand, as they are also produced. This is a clear advantage from a processing/economical point of view.

For a continuous process, the feed to the reactor system preferably comprises a carbohydrate source dissolved an aqueous liquid, a regenerated tungsten-containing compound (preferably solubilized in an alkylene glycol as set out above), and hydrogen.

In the present invention, it is preferred that the tungsten-containing compound in the reactor system comprises tungstic acid ($H_2WO_4$), a tungstate salt, tungsten oxide or mixtures thereof, wherein the tungstate salt is preferably an alkali metal tungstate. This will most likely also be the form of the tungsten-containing compound in the reactor effluent, and also in the polyol bottom stream. Burning such polyol bottom stream may lead to conversion of one tungsten containing compound in another one. Regeneration may involve bring the tungsten-containing compound back into the chemical composition desired for use in the reaction concerned.

The reactor may also produce off-gas, which may contain both unreacted hydrogen, but also other components like lower alkanes. Such off-gas may also conveniently be disposed off through the burner. Hence, in the process according to the present invention it is preferred that the reactor contains an outlet for gaseous compounds, which gaseous compounds are also fed to the burner of step b.

Burning is carried out at a temperature above 900° C. to achieve complete burning of all organic components. Lower temperatures may result in too high levels of carbon monoxide or other undesired components. Preferably, the polyols in the present invention are burned in step b. at a temperature of above 1000° C., preferably above 1100° C.

The reactor in which the hydrogenolysis is carried out is preferably a continuously stirred tank reactor. For hydrogenolysis according to the present invention the temperature in the reactor is typically between 120° and 300° C., and hydrogen partial pressure is typically between 1 and 6 MPa.

The feed to the reactor preferably comprises a stream comprising from 40 to 90% (by weight based on the total weight of the feed) of water, preferably the feed comprises from 50 to 80% (by weight based on the total feed) of water. Such stream preferably comprises from 10 to 40% (preferably from 15 to 30%, by weight on such feed) of a carbohydrate. Suitable carbohydrates include sugars (e.g. mono- and disaccharides), cellulose and cellulose-derivatives such as hydrolysates, hemicellulose and hemi-cellulose derivatives such as hydrolysates.

The hydrogenolysis metal used as co-catalyst in the present reaction (the heterogeneous catalyst) is preferably selected from the groups 8, 9 or 10 of the Periodic Table of Elements. More preferably, such is selected from the group consisting of Cu, Fe, Ni, Co, Pd, Pt, Ru, Rh, Ir, Os, and combinations thereof, and most preferably selected from Ru and Rh. The hydrogenolysis metal is preferably present in the form of a catalyst supported on a carrier.

In a continuous reaction according to the present invention, there is a continuous feed (e.g of carbohydrates dissolved in an aqueous liquid, as well as hydrogen) but also a continuous effluent or product stream. Part of the reactor effluent or product stream out of the reactor is also the homogeneous catalyst, in the present invention the tungsten-containing compound. This means that continuously, or periodically, such homogeneous catalyst needs to be added to the reactor as well. Hence, in the present invention it is preferred that the tungsten-containing compound of the catalyst system is continuously or periodically added to the reactor. Such addition can be combined with the carbohydrates in aqueous liquid, or it can be added to the reactor as a separate stream.

The tungsten-containing compound of the catalyst system which is added to the reactor is preferably obtained from the ash of step c., optionally after regeneration.

In the process according to the present invention, it is preferred that no polyols from the bottoms streams of the distillation stages are fed back to the reactor, as such may lead to build-up of polyols and/or their degradation products, making the process more difficult to control.

EXAMPLE

A simulation was done using Aspen software for hydrogenolysis of sucrose with hydrogen using tungstic acid as catalyst in a continuous process.

Products aimed for by distillation were ethylene glycol (EG), propylene glycol (PG) and part of the glycerol produced, all three with a purity above 99%.

All amounts were normalized to production of 1 ton ethylene glycol per time unit produced after purification by distillation.

A reactor R1 with the following feeds:

sucrose (2.431 ton) in water (7.288 ton)

hydrogen (0.117 ton)

crude ethylene glycol (1.733 ton) (organic solvent) with solubilized therein tungstic acid (0.048 ton)

Flow out of the reactor R1 was subjected to a series of separation steps: evaporation of water and aliphatic alcohols, distillation of EG, PG, part of the glycerol and a bottom stream. The bottom stream included part of the glycerol not isolated substantially pure form, other C3-C6 polyols, as well as small amounts of EG, PG, and 1,2 BG, and solubilized tungstic acid. This gave after separation:

off gas (aliphatic alcohols, alkanes, hydrogen)

water aliphatic alcohols ethylene glycol (>99% pure)

propylene glycol (>99% pure)

glycerol (>99% pure)

bottom stream with C3-C6 polyols (including part of the glycerol not isolated substantially pure form) with solubilized therein tungstic acid.

Part of crude ethylene glycol produced in distillation was used for solubilizing tungstic acid, for recycling back to the reactor R1.

To the burner of a boiler system were fed:

the off gas from reactor R1 the aliphatic alcohols of R1 the C3-C6 polyols bottom stream of distillation of EG, PG, and glycerol, with solubilized therein tungstic acid EG/BG azeotrope from distillation.

To the boiler was fed: 5.523 ton of water, which was converted into steam by heat from the burner. The steam generated by the boiler was used to drive (part of) evaporation of water from the reactor products and distillation.

From the boiler was isolated: ash containing a tungsten-containing compound. The tungsten-containing compound in the ash was recovered and regenerated into tungstic acid and solubilized in part of the (crude) ethylene glycol produced. This resulted in an energy balance as in table 1.

TABLE 1

| process unit | source | energy flow IN (GJ/ton EG) | energy flow OUT (GJ/ton EG) |
|---|---|---|---|
| reactor 1 feed | streams | −144.7 | −143.3 |
| | equipment | 4.6 | 3.2 |
| evaporation | streams | −143.1 | −148.3 |
| | equipment | 15.7 | 20.9 |
| distillation | streams | −30.6 | −31.2 |
| | equipment | 17.2 | 17.6 |
| boiler + burner | streams | water feed to boiler: −84.2 | steam produced: −71.5 |
| | | offgas: −1.8 | flue gas: −18.6 |
| | | | solid ash with W: −0.2 |

8

TABLE 1-continued

| process unit | source | energy flow IN (GJ/ton EG) | energy flow OUT (GJ/ton EG) |
|---|---|---|---|
| tungsten cat recovery | | polyols: −2.6 | |
| | | air: −0.1 | |
| | equipment | 0.2 | 0.1 |
| | streams | −4.6 | −5.1 |
| | equipment | 0.003 | 0.5 |
| total | | −373.9 | −375.5 |

Calculation error: 0.5%

The above shows that when burning a polyol bottom stream of distillation of reaction products from hydrogenolysis of sucrose in a boiler system, this generates a lot of steam which can be utilized driving part of the evaporation and distillation required, as well as that it allows recovery of tungsten-containing catalyst material.

The invention claimed is:

1. A process for producing ethylene glycol and/or propylene glycol and/or glycerol in a continuous manner from a feed to a reactor, the feed comprising a carbohydrate source in an aqueous liquid, hydrogen, and a cocatalyst comprising a tungsten-containing compound, said reactor comprising a further co-catalyst comprising a metal selected from the groups 8, 9, or 10 of the Periodic Table of Elements, wherein the flow out of the reactor comprises water, the tungsten containing compound, one or more of ethylene glycol, propylene glycol, glycerol, and one or more polyols other than glycerol, wherein said flow out of the reactor is subjected to the following process steps:

a. separating ethylene glycol and/or propylene glycol and/or glycerol from the flow out of the reactor to yield ethylene glycol and/or propylene glycol and/or glycerol and one or more bottom streams comprising polyols and one or more tungsten-containing compounds, b. subjecting said bottom streams of distillation stages to a burner in which the polyols are burned at a temperature of above 900° C., c. recovering ash comprising a tungsten-containing compound from one or more of: the burner, ancillary parts of the burner, the exhaust gas, d. recovering recover at least part of the tungsten-containing compound from the recovered ash obtained by step c., wherein said burner is part of a boiler system to generate steam from water.

2. The process according to claim 1, wherein the separation of ethylene glycol and/or propylene glycol and/or glycerol of the flow out of the reactor in step a. is effected by distillation.

3. The process according to claim 1, wherein the steam generated in the boiler is used in the separation of the ethylene glycol and/or propylene glycol and/or glycerol of the flow out of the reactor.

4. The process according to claim 1, wherein the tungsten-containing compound recovered from the ash is regenerated and solubilised in a liquid for feeding back to the reactor.

5. The process according to claim 4, wherein the liquid in which the regenerated tungsten-containing compound is solubilized comprises alkylene glycol.

6. The process according to claim 1, wherein the feed into the reactor system comprises a carbohydrate source dissolved an aqueous liquid, a regenerated tungsten-containing compound, and hydrogen.

7. The process according to claim 1, wherein the tungsten-containing compound in the reactor system comprises tungstic acid (H2WO4), a tungstate salt, tungsten oxide or mixtures thereof.

8. The process according to claim 1, wherein prior to or during step a. volatile alcohols comprising ethanol and/or methanol are removed from the flow out of the reactor, which volatiles are also fed to the burner of step b.

9. The process according to claim 1, wherein prior to step a. water is removed from the flow out of the reactor system by evaporation.

10. The process according to claim 1, wherein the reactor contains an outlet for gaseous compounds, which gaseous compounds are also fed to the burner of step b.

11. The process according to claim 1, wherein the polyols are burned in step b. at a temperature of above 1000° C.

12. The process according to claim 1, wherein the reactor is a continuously stirred tank reactor.

13. The process according to claim 1, wherein the hydrogenolysis metal selected from the groups 8, 9, or 10 of the Periodic Table of Elements is selected from the group consisting of Cu, Fe, Ni, Co, Pd, Pt, Ru, Rh, Ir, Os, and combinations thereof.

14. The process according to claim 1, wherein said tungsten-containing compound of the catalyst system is continuously or periodically added to the reactor.

15. The process according to claim 1, wherein the tungsten-containing compound of the catalyst system added to the reactor is obtained from the ash of step c., optionally after regeneration.

16. The process according to claim 3, wherein the steam generated in the boiler is used in the separation of the ethylene glycol and/or propylene glycol and/or glycerol of the flow out of the reactor by using the steam in distillation of one or more of ethylene glycol and/or propylene glycol and/or glycerol from the flow out of the reactor.

17. The process according to claim 5, wherein the liquid in which the regenerated tungsten-containing compound is solubilized comprises ethylene glycol and/or propylene glycol.

18. The process according to claim 7, wherein the tungsten-containing compound in the reactor is an alkali metal tungstate.

19. The process according to claim 11, wherein the polyols are burned in step b. at a temperature of above 1100° C.

20. The process according to claim 13, wherein the hydrogenolysis metal selected from the groups 8, 9, or 10 of the Periodic Table of Elements is selected from Ru and Rh.

* * * * *